(12) United States Patent
Jarrell

(10) Patent No.: US 8,973,427 B2
(45) Date of Patent: Mar. 10, 2015

(54) APPARATUS AND METHODS FOR THE MEASUREMENT OF MASS RELATED PARAMETERS

(75) Inventor: Joseph A. Jarrell, Newton Highlands, MA (US)

(73) Assignee: Waters Technologies Corporation, Milford, MA (US)

(*) Notice: Subject to any disclaimer, the term of this patent is extended or adjusted under 35 U.S.C. 154(b) by 1032 days.

(21) Appl. No.: 13/058,549

(22) PCT Filed: Aug. 7, 2009

(86) PCT No.: PCT/US2009/053068
§ 371 (c)(1),
(2), (4) Date: Apr. 29, 2011

(87) PCT Pub. No.: WO2010/019455
PCT Pub. Date: Feb. 18, 2010

(65) Prior Publication Data
US 2011/0271755 A1 Nov. 10, 2011

Related U.S. Application Data

(60) Provisional application No. 61/089,203, filed on Aug. 15, 2008.

(51) Int. Cl.
*G01H 13/00* (2006.01)
*G01N 9/00* (2006.01)
(Continued)

(52) U.S. Cl.
CPC .......... *G01N 30/62* (2013.01); *G01N 2030/027* (2013.01); *G01N 30/8631* (2013.01); *G01N 2009/004* (2013.01); *G01H 13/00* (2013.01); *G01N 9/002* (2013.01)

USPC ......... 73/61.49; 73/32 A; 73/54.41; 73/61.52; 73/64.53; 73/580

(58) Field of Classification Search
CPC ....... G01H 13/00; G01N 9/002; G01N 30/62; G01N 30/8631; G01N 30/8634; G01N 30/8637; G01N 2009/004; G01N 2030/027
USPC ......... 73/32 A, 54.41, 61.49, 61.52, 73/61.55–61.56, 61.79, 64.53, 580
See application file for complete search history.

(56) References Cited

U.S. PATENT DOCUMENTS 2,635,462 A 4/1953 Poole et al.
2,865,201 A * 12/1958 Roth ........................ 73/861.355
(Continued)

FOREIGN PATENT DOCUMENTS

WO PCT/ISA/210 9/2009
WO PCT/ISA/237 7/2010

OTHER PUBLICATIONS

Lu, Chih-shun, "Mass determination with piezoelectric quartz crystal resonators"; Vac. Sci. Technol., vol. 12, No. 1, Jan./Feb. 1975; p. 578-583.
Son, Sungmin, et al., "Suspended Microchannel Resonators for Ultralow Volume Universal Detection"; Anl. Chem., vol. 80, No. 12, Jun. 15, 2008, p. 4757-4760.
(Continued)

*Primary Examiner* — Thomas P Noland
(74) *Attorney, Agent, or Firm* — Waters Technologies Corporation

(57) ABSTRACT

Embodiments of the present invention are directed to resonating detection devices in which the sample flows through a conduit having a section in which the conduit is grouped or concentrated with the point of maximum movement. An exemplary device includes a primary conduit, at least one first flex section, at least one second flex section and at least one analysis section. The primary conduit cooperates with an energizer for inducing vibration and a programmed calculator for determining a resonant frequency to calculate a mass related parameter of the solution carried therein.

34 Claims, 6 Drawing Sheets

(51) Int. Cl.
    *G01N 30/02*     (2006.01)
    *G01N 30/62*     (2006.01)
    *G01N 30/86*     (2006.01)

(56) References Cited

U.S. PATENT DOCUMENTS

| | | | | |
|---|---|---|---|---|
| RE31,450 | E * | 11/1983 | Smith | 73/32 A X |
| 4,422,338 | A * | 12/1983 | Smith | 73/861.356 |
| 5,423,221 | A | 6/1995 | Kane et al. | |
| 5,557,973 | A | 9/1996 | Koudal et al. | |
| 6,942,169 | B2 | 9/2005 | Sparks | |
| 7,228,735 | B2 | 6/2007 | Sparks et al. | |
| 7,263,882 | B2 | 9/2007 | Sparks et al. | |
| 7,282,329 | B2 | 10/2007 | Manalis et al. | |
| 7,387,889 | B2 | 6/2008 | Manalis | |
| 8,312,763 | B2 * | 11/2012 | Manalis et al. | G01N 9/002 |
| 2004/0038426 | A1 | 2/2004 | Manalis | |
| 2007/0157739 | A1 | 7/2007 | Sparks et al. | |
| 2008/0053240 | A1 * | 3/2008 | Henry et al. | G01N 9/002 |

OTHER PUBLICATIONS

Trathnigg, Bernd, et al., New Universal Detector for High-Performance Liquid Chromatography: The Density Detector; Journal of Chromatography, 385 (1987) 17-23, pp. 17-23.

Burg, Thomas P. et al., "Weighing of biomolecules, single cells and single nanoparticles in fluid; Nature, vol. 446/26 Apr. 2007, doi:10.1038/nature05741, pp. 1066-1069".

Burg, Thomas P. et al., "Weighing of Biomolecules, Single Cells, and Single Nanoparticles in Fluid"; Nature, doi:10.1038/nature05741; pp. 1-6, Supplementary Methods and Discussion, Apr. 2007.

Burg, Thomas P. et al, "Vacuum-Packaged Suspended Microchannel Resonant Mass Sensor for Biomolecular Detection", Journal Of Microelectromechanical Systems, 2006, pp. 1-10.

Burg, Thomas P., "Suspended Microchannel Resonators for Biomolecular Detection"; Massachusetts Institute of Technology, Sep. 2005, pp. 3-124, of Ph. D thesis.

Burg, T. P. et al., Suspended microchannel resonators for biomolecular detection; Applied Physics Letters, vol. 83, No. 13, Sep. 29, 2003, pp. 2698-2700.

\* cited by examiner

APPARATUS AND METHODS FOR THE MEASUREMENT OF MASS RELATED PARAMETERS

RELATED APPLICATIONS

This application is the U.S. national stage of International Application No. PCT/US2009/053068, filed Aug. 7, 2009 and designating the United States, which claims priority to U.S. Provisional Patent Application Ser. No. 61/089,203, filed Aug. 15, 2008, the entire contents of which are incorporated herein by reference.

FIELD OF THE INVENTION

Embodiments of the present invention relate to resonating cantilever arms for measuring changes in mass related parameters.

FEDERAL SPONSORSHIP

This invention was not developed with Federal sponsorship.

BACKGROUND OF THE INVENTION

Embodiments of the present invention are directed devices which induce movement in cantilevered arms. Such devices measure changes in resonance of such arms upon changes in mass. These changes in resonance are used to determine mass related parameters. As used herein, the term "mass related parameters" refers to values which can be measured or calculated from such changes in resonance in cantilevered arms induced or caused by a change in the mass carried by such arm.

Embodiments of the present invention have particular applications in measuring fluids contained or flowing in microfluidic devices. As used herein, the term "microfluidic" refers to devices which contain approximately 10 micro-liters or less.

As used herein, the term "analyte" refers to a compound or composition which is of interest. By way of example, without limitation, such analyte can be a compound for which information as to its presence or absence is desired, or its concentration, or the mass of the compound in the solution in which it is dissolved.

As used herein, the term "solute" refers to a compound that is dissolved. The compound or mixture of compounds in which the solute is dissolved is the solvent.

Chromatography is a technique in which compounds held in solution are separated from each other by the different affinity such compounds exhibit to a media held stationary or moving in a different manner than the solution in which the compounds are held. High performance liquid chromatography (HPLC) uses pressure to compel solutions carrying compounds of interest through an immobilized media of packed particles or functional equivalent or a monolith plug of porous material. The immobilized media is often referred to as the stationary phase. A compound which exhibits affinity for a stationary phase will leave the stationary phase, and elute, as a concentration of the compound in the solution. Detectors of the compound measure the concentration as a peak. Chromatographic systems are known in the art and generally comprise a pump, sample injector and detectors. Such systems are available from several vendors.

Presently, there is a need for devices and methods that will provide a analytical value relating to mass of a compound that can be used with separations techniques such as chromatography.

SUMMARY OF THE INVENTION

Embodiments of the present invention feature devices and methods that will provide an analytical value relating to mass of a compound. The devices and methods of the present invention are well suited for use in conjunction with other analytical techniques such as chromatography. One embodiment of the present invention features a device for performing an analysis of a solution. The device has a primary conduit having a first fixed end, second fixed end, at least one first flex section, at least one second flex section and at least one analysis section. The first fixed end and the second fixed end are each for attachment to a base. The first flex section has a first flex section length and, similarly, the second flex section has a second flex section length. The first flex section and the second flex section define a motion point distal to the first end and said second end in which the primary conduit has the greatest degree of motion. The motion point is for vibrating at a resonant frequency determined by the mass of the primary conduit and solutions carried with the primary conduit. The primary conduit has a first channel defining a fluid path for receiving said solutions. The first channel has an inlet, and an outlet. The first inlet is at the first fixed end and the first outlet is at the second fixed end. The first analysis section has at least one curve about the motion point and has an analysis length. The analysis length exceeds at least one half of one of the first flex section length and the second flex section length. The first conduit is for cooperating with means for inducing vibration and means for determining a resonant frequency to calculate a mass related parameter of the solution carried therein.

The analysis section focuses the mass of solutions carried in the channel to the motion point providing increased sensitivity to changes in the solution mass.

One embodiment of the present invention features a primary conduit having a first arm. The first arm has a first length, first distal end, and a first proximal end. The length is the distance between the first proximal end and the first distal end. The first proximal end is attached or constructed and arranged to attach to a base. The first distal end is free for vibrating at a resonant frequency determined by the mass of the primary conduit and solutions carried therein. The analytical section of the first channel concentrates or gathers the first channel at the distal end of the arm to increase sensitivity of the arm to changes in mass caused by different concentrations of solute in the solutions.

One preferred device has an analysis section in the form of a coil or serpentine pattern. Preferably, the coil or serpentine pattern is substantially aligned with the motion point. This alignment places a large volume of fluid potentially containing an analyte in the channel where the device is most sensitive to changes in mass. Embodiments featuring a arm place the coil or serpentine pattern close or at the most distal end. Preferably, the coil or serpentine pattern is placed within the last twenty five percent of the arm.

One preferred device further comprises energy means for inducing vibration in the first arm. As used herein, "energy means for inducing vibration" comprise mechanical, electrical, optical, acoustic, and magnetic mechanisms for imparting kinetic energy to the primary conduit setting the primary conduit in motion. The primary conduit, in response to the periodic application of such energy, will exhibit a resonant frequency in which the energy to induce and maintain such motion is most efficient. The means for inducing vibration in the primary conduit is, preferably, capable of being placed or is placed in signal communication with determining means for determining a resonant frequency of the primary conduit.

A preferred device further comprises determining means for determining the resonant frequency of the primary conduit. The determining means for determining the resonant frequency is preferably in signal communication with the energy means for inducing vibration in the primary conduit. For example, without limitation, the determining means monitors and/or controls the phase difference between the energy means and the determining means. Thus, determining means comprises sensors for detecting the movement of the first arm and/or energy consumption of the energy means, and computational processing units (CPUs) for processing the signals and data. A preferred determining means compares the resonant frequency or the energy consumption of the primary conduit in the presence or potential presence of an analyte and compares the value to a standard. The comparison relates to the density and/or mass of one or more solutions flowing through the first channel.

One preferred device features a primary conduit as described and further comprises a secondary conduit. The secondary conduit is in fluid communication with the primary conduit. The secondary conduit has a secondary first fixed end, a secondary second fixed end, at least one secondary first flex section and at least one secondary second flex section. The secondary first fixed end and the secondary second fixed end are each for attachment to a base. The secondary flex section has a secondary flex section length and, similarly, the secondary second flex section has a secondary second flex section length. The secondary first flex section and secondary second flex section define a secondary motion point distal to the secondary first end and the secondary second end in which the secondary conduit has the greatest degree of motion. The motion point is for vibrating at a resonant frequency determined by the mass of the secondary conduit and solutions carried with the secondary conduit. The secondary conduit has a secondary channel defining a fluid path for receiving the solutions. The secondary channel has a secondary inlet, a secondary outlet, and at least one secondary analysis section. The first inlet is at the secondary first fixed end and the first outlet at the secondary second fixed end. The secondary analysis section spans therebetween and defines a secondary channel volume. The second channel volume is smaller than the volume of the primary analysis section to allow measurement of mass parameters of a solution in the presence and absence of a peak in the first channel and the second channel.

Preferably, the second conduit allows measurement of at least one mass parameter of a solution in which the analyte is the present in at least one of the first channel and second channel and absent in the other. Thus, the difference in mass of the analyte can be directly related to the differences in resonance of the primary conduit.

Preferably, the embodiments further comprise energy means for inducing vibration in said second arm and further determining means for determining the resonant frequency of said second arm. Preferably, such determining means determines a mass change related to the presence of an analyte in accordance with the equation:

$$\frac{\delta \omega_0}{\omega_0} \propto -\frac{\delta m}{m}$$

Where $\omega_0$ is the resonant frequency of the device in the absence of analyte, $\delta\omega_0$ is the change in resonant frequency observed when an analyte is present within the device, m is the mass of the device and $\delta m$ is the change in mass of the device when analyte is present.

A further embodiment of the present invention is directed to a method for measuring changes in a solution. The method comprises the steps of providing a device having a primary conduit having a first fixed end, second fixed end, at least one first flex section, at least one second flex section and at least one analysis section. The first fixed end and the second fixed end are each for attachment to a base. The first flex section has a first flex section length and, similarly, the second flex section has a second flex section length. The first flex section and second flex section define a motion point distal to the first end and the second end in which the primary conduit has the greatest degree of motion. The motion point is for vibrating at a resonant frequency determined by the mass of the primary conduit and solutions carried with the primary conduit. The primary conduit has a first channel defining a fluid path for receiving solutions. The first channel has an inlet, an outlet. The first inlet is at the first fixed end and the first outlet at the second fixed end. The first analysis section has at least one curve comprising the first channel about the motion point and having an analysis length. The analysis length exceeds at least one half of one of the first conduit length and said second conduit length. The first conduit is for cooperating with means for inducing vibration and means for determining a resonant frequency to calculate a mass related parameter of the solution carried therein. The method further comprises the step of inducing vibration of the primary conduit and determining a resonant frequency of said first conduit as a function of the solutions flowing there through.

Embodiments of the present method feature devices in which the analysis section has a larger volume than the channel positioned towards the proximal end. The volume of the analytical section, preferably, is larger by at least twenty percent the volume of the first channel that is not in the analytical section. A preferred method features a first channel having an analytical section that is in a serpentine or coil pattern. The coil or serpentine pattern places the analyte in solution about the longest arc of the arm, preferably, towards the last twenty five percent of the length of first arm, substantially corresponding to said longest arc at said distal end.

Embodiments of the present method are well suited for analysis in conjunction with high performance liquid chromatography. Preferably, the first analysis section has a first analysis section volume and said first analysis section volume serves to focus the peak in the first analysis section.

A further embodiment of the present method features a device having a primary conduit and a secondary conduit. The secondary conduit is in fluid communication with the primary conduit. The secondary conduit has a secondary first fixed end, a secondary second fixed end, at least one secondary first flex section and at least one secondary second flex section. The secondary first fixed end and the secondary second fixed end are each for attachment to a base. The secondary flex section has a secondary flex section length and the secondary second flex section has a secondary second flex section length. The secondary first flex section and secondary second flex section define a secondary motion point distal to the secondary first end and the secondary second end in which the secondary conduit has the greatest degree of motion. The motion point is for vibrating at a resonant frequency determined by the mass of said secondary conduit and solutions carried with the secondary conduit. The secondary conduit has a secondary channel defining a fluid path for receiving the solutions. The secondary channel has an secondary inlet, an secondary outlet, and at least one secondary analysis section. The first inlet is at the first fixed end and the first outlet is at the second fixed end. The secondary analysis section spans therebetween and defines a secondary channel volume. The second channel volume is smaller than the volume of the primary analysis section to allow measurement of mass parameters of a solution in the presence and absence of a peak in said first channel and said second channel. And, the method comprises the step of identifying at least one peak in said secondary conduit to allow determinations as to the mass of an analyte.

Preferably, the secondary conduit and primary conduit are used with energy means and determining means. And, preferably, the method comprises the step of comparing the resonant frequency of the secondary conduit to the resonant frequency of the primary to determine the mass of one or more analytes flowing there through.

Preferably, such determining means determines a mass change related to the presence of an analyte in accordance with the equation:

$$\frac{\delta \omega_0}{\omega_0} \propto -\frac{\delta m}{m}$$

Where $\omega_0$ is the resonant frequency of the device in the absence of analyte, $\delta\omega_0$ is the change in resonant frequency observed when an analyte is present within the device, m is the mass of the device and $\delta m$ is the change in mass of the device when analyte is present.

These and other features and advantages of the present invention will be apparent to those skilled in the art upon viewing the drawing and reading the detailed descriptions that follow.

DETAILED DESCRIPTION OF THE INVENTION

Embodiments of the present invention will be described in detail with respect to preferred embodiments that feature devices and methods that provide an analytical value relating to mass of a compound. These devices and methods are well suited for use in conjunction with other analytical techniques such as chromatography but also for process controls in industrial processes.

Figure 1:
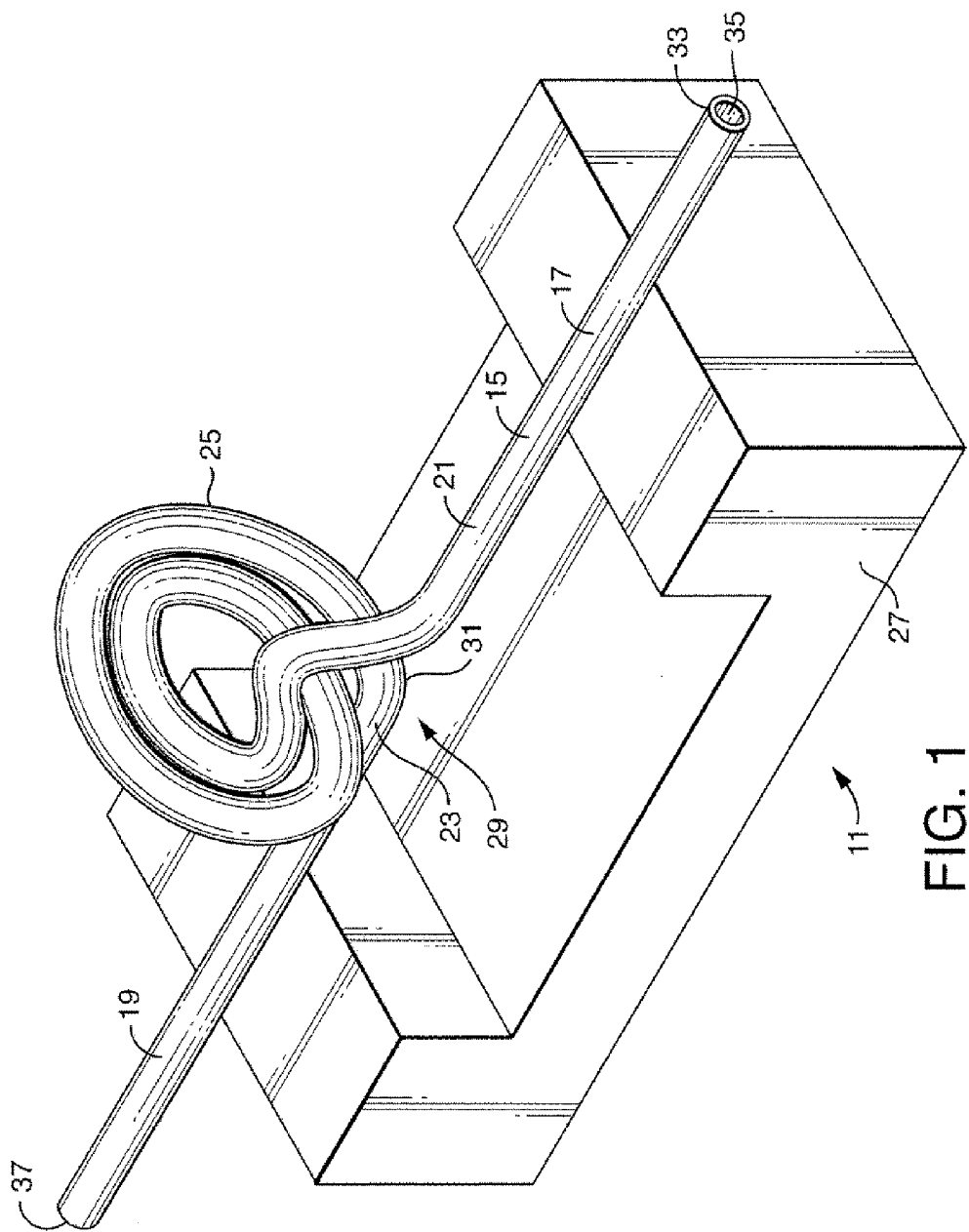
FIG. 1 depicts a device embodying features of the present invention.

Turning first to FIG. 1, a device, for performing an analysis of a solution, embodying features of the present invention, generally designated by the numeral 11, is depicted. The device 11 has a primary conduit 15 having a first fixed end 17, second fixed end 19, at least one first flex section 21, at least one second flex section 23, and at least one analysis section 25. The first fixed end 17 and the second fixed end 19 are each for attachment to a base 27.

The base 27 is a solid mass intended to resist motion and vibration such that the first flex section 21 and the second flex section 23 are capable of movement and the first fixed end 17 and second fixed end 19 are substantially stationary. Thus, base 27 is selected to be relatively more massive and rigid than primary conduit 15. Preferred materials for the base 27 include silica, metal and/or ceramic materials. Primary conduit 15 is preferably made of a material such as silica, metal, or ceramic.

The first flex section 21 has a first flex section length and, similarly, the second flex section 23 has a second flex section length. As depicted, the first flex section 21 and second flex section 23 are substantially equal in length but do not need to be as long as the primary conduit has freedom to move. This movement is preferably a vibrating motion, in which the primary conduit 15 moves radially about its axis or twists or rotates about an axis defined by the primary conduit 15. The first flex section 21 and the second flex section 23 define a motion point 29, apart from and distal to the first end 17 and said second end 19. The motion point 29 is the place in which the primary conduit 15 has the greatest degree of motion. The motion point 29 is for vibrating at a resonant frequency determined by the mass of the primary conduit 15 and solutions carried with the primary conduit 15.

The first analysis section 25 has at least one curve 31 about the motion point and has an analysis length. The curve 31 can carry forward along a section of the primary conduit 15 to form a coil, as illustrated, or comprise many curves folding the primary conduit 15 in to a serpentine pattern to be described more fully with respect to other embodiments. The analysis length exceeds at least one half, one of the first flex section 21 length and the second flex section 23 length. The analysis section 25 focuses the mass of solutions carried in the primary conduit to the motion point providing increased sensitivity to changes in the solution mass. Longer analysis lengths, for example where the analysis length is at least as long as one of said first flex section 21 length and second flex section 23 length, allow for a sample of larger size. In applications where the device 11 is used with chromatographic systems [not shown], the analysis section 25 may have a length to define a volume that corresponds to a fraction of the volume of an analyte peak. An increase in the length of the analyte section 25 equaling or exceeding the volume of an analytical peak of a chromatography system, by five to twenty percent, is useful to ensure capture of the entire sample.

The primary conduit 15 has a first channel 33 defining a fluid path for receiving said solutions. The first channel 33 has a first inlet 35 and a first outlet 37. The first inlet 35 is at the first fixed end 17 and the first outlet 37 is at the second fixed end. The first conduit 15 is for cooperating with energy means [not shown] for inducing vibration and determining means [not shown] for determining a resonant frequency to calculate a mass related parameter of the solution carried therein. As used herein, energy means comprise mechanical, acoustic, optical, electrical, magnetic elements which impart kinetic energy to the primary conduit. The primary conduit 15 may comprise elements such as wires, magnetic, mechanical, or optical elements to facilitate the transfer of energy to the primary conduit 15 from the base 25.

As used herein, the determining means refers to a sensors [not shown] and readers [not shown] for determining the resonant frequency of the primary conduit 15 as solutions and samples flow through the first channel 33. These sensors and readers are normally in signal communication with computational processing units (CPUs) [not shown] known in the art. CPUs are commonly integrated with instruments and computers, including by way of example personal, mainframe, servers and the like. As used herein, the term "signal communication" refers to being able to transmit or send or receive information in the form of electro magnetic or photo-optical transmissions or wired for direct transmission.

Embodiments of the present invention can be built on a microfluidic scale and incorporated in microfluidic instruments and chromatographic systems.

Figure 2:
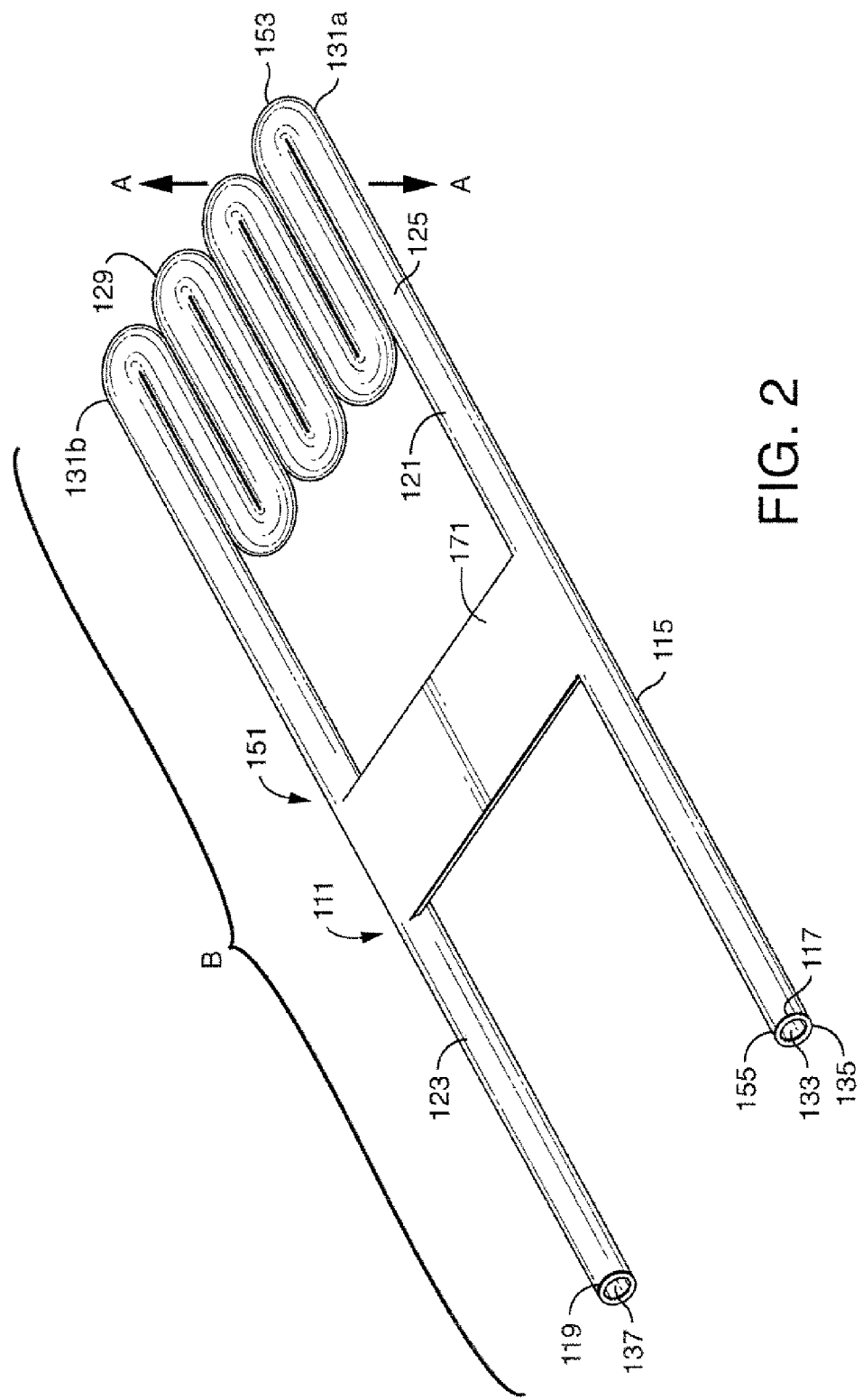
FIG. 2 depicts a device embodying features of the present invention.

Turning now to FIG. 2, a further embodiment of the present invention, generally designated by the numeral 111, is depicted. Device 111 has a primary conduit 115 having or in the form of a first arm, generally designated by the numeral 151. The first arm 151 has a first length, first distal end 153, and a first proximal end 155. The first length is the distance between the first proximal end 155 and the first distal end 153 denoted by bracket B. The first proximal end 155 is attached to or constructed and arranged to attach to a base [not shown]. The first distal end 153 is free for vibrating at a resonant frequency determined by the mass of the primary conduit and solutions carried therein. The distal end 153 corresponds to the motion point 129.

The primary conduit 115 has a first fixed end 117, second fixed end 119, at least one first flex section 121, at least one second flex section 123, and at least one analysis section 125. The analytical section 125 of the primary conduit 115 begins and ends at about the first curve 131a and last curve 131b in a series of curves and bends [not all are numbered for the purpose of clarity] to concentrate or gather the primary conduit 115 at the distal end 153 of the arm 151. As depicted in FIG. 2, the primary conduit 115 is in the form of a serpentine pattern, however a coil or a combination of a coil and serpentine pattern or a random pattern which localizes the primary conduit 115 at the distal end 153 may be used. Concentrating the primary conduit 115 at the distal end 153 increases the sensitivity of the arm 151 to changes in mass caused by different concentrations of solute in the solutions. Preferably, the coil or serpentine pattern of the analytical section 125 is placed within the last twenty five percent of the length of the arm 151. Additionally the internal diameter of conduit 115 within flex sections 121 and 123 may be substantially less than its internal diameter within the analytical section 125. In another embodiment, the analytical section 125 of primary conduit 115 may comprises a portion where the outer diameter of conduit 115 is substantially larger that its outside diameter in the flex sections 121 and 123. the transitions between these sections of differing inner and/or outer diameter may be discrete or continuous.

One or more cross-members 171 are attached between flex sections 121 and 123 of which only one is shown. Cross member 171 serves to reduce any twisting modes of vibration of the device in which the flex sections 121 and 123 would move in opposite directions.

Figure 3:
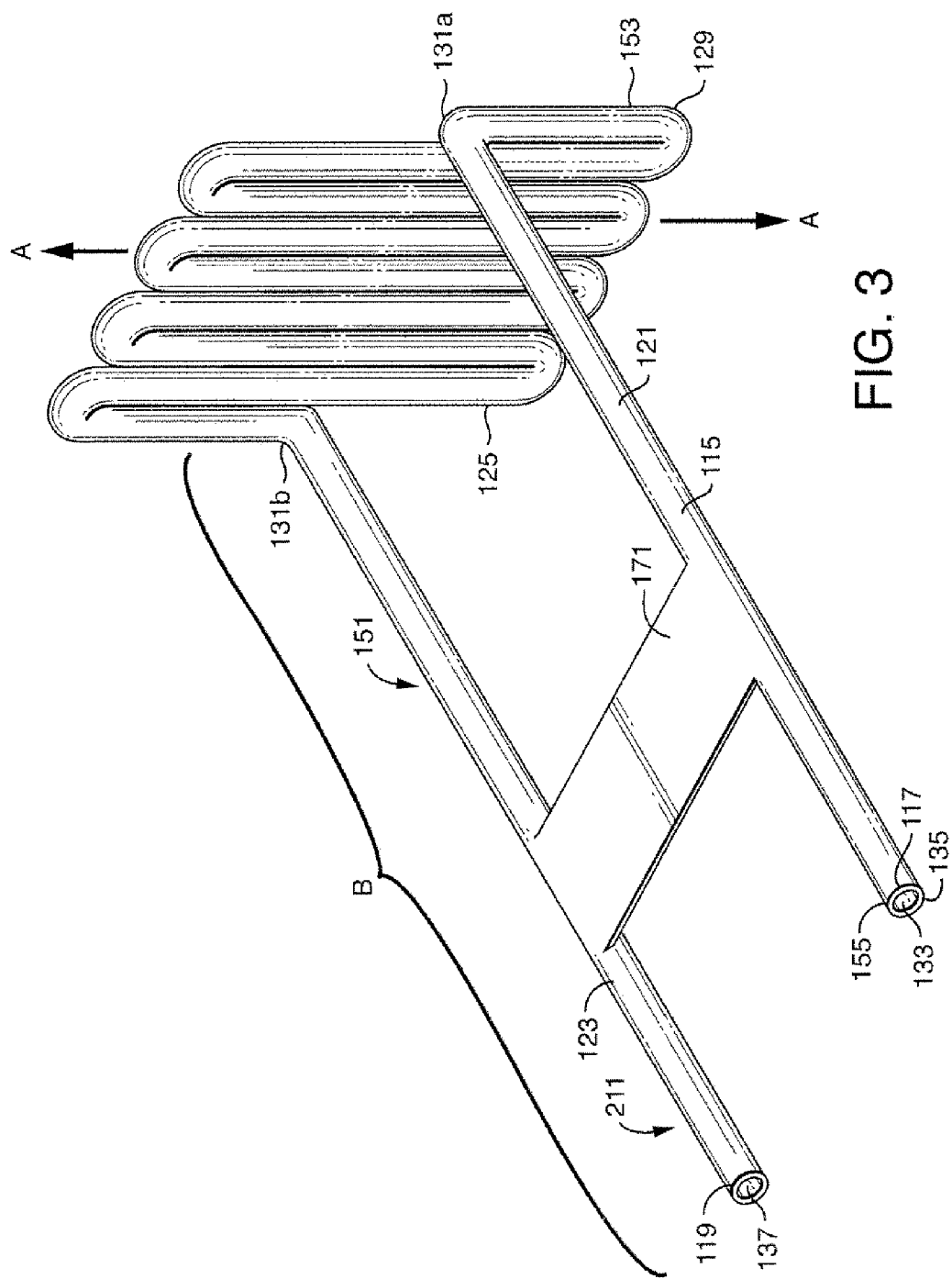
FIG. 3 depicts a device embodying features of the present invention.

FIG. 3 depicts a device 211, similar to device 111 of FIG. 2 such that all similar elements will be referred to with common numerical designations. FIG. 3 depicts a device 211 in which the analytical section 125 is further aligned with the motion point 129 by concentrating the primary conduit 115 in plane substantially tangential to the arc of movement, denoted by arrows A-A. This alignment places a large volume of fluid potentially containing an analyte in the analytical section 125 where the device 211 is most sensitive to changes in mass. Embodiments featuring a arm place the coil or serpentine pattern close to or at the most distal end.

Figure 4:
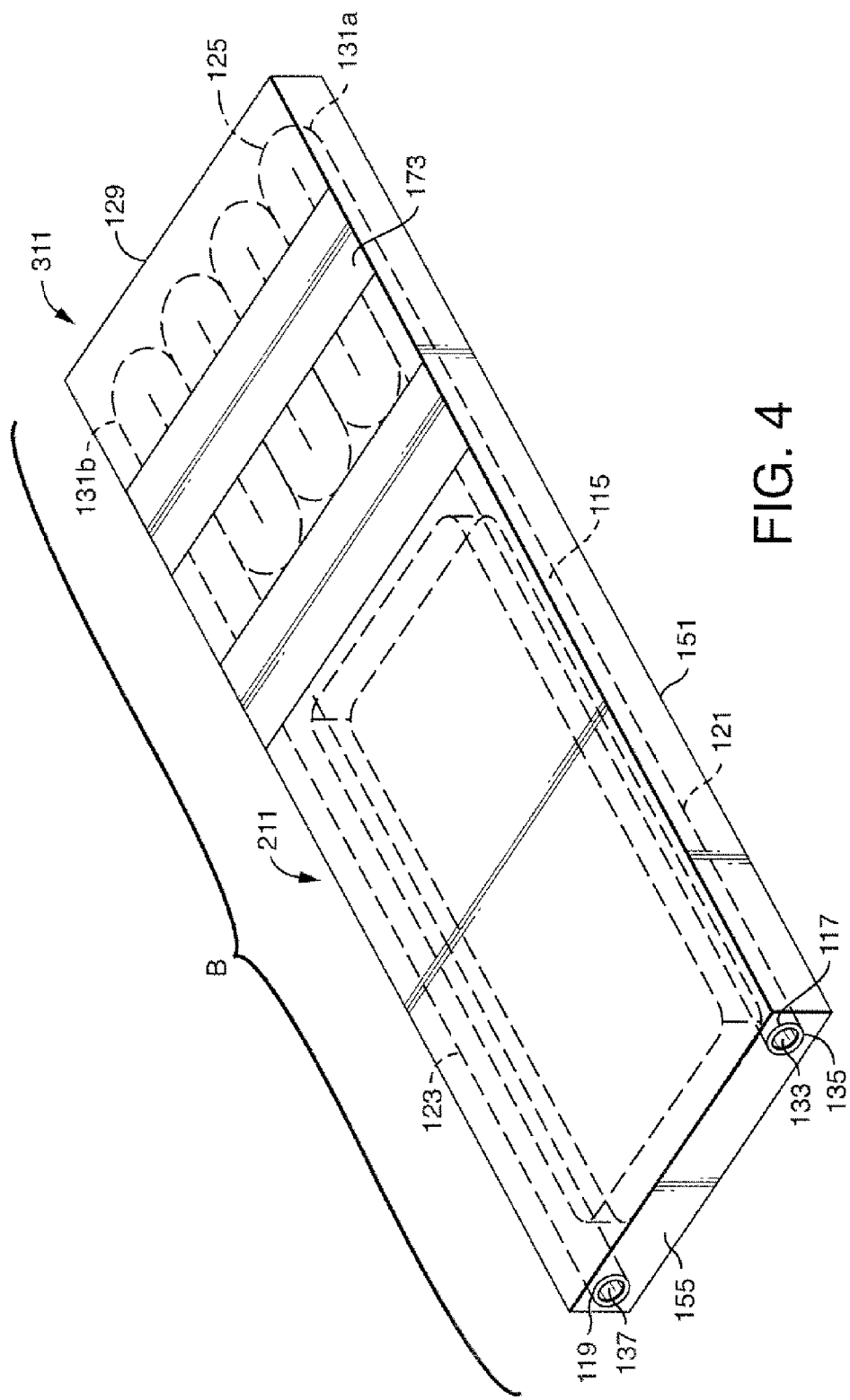
FIG. 4 depicts a device, in partial cross section, embodying features of the present invention.

Embodiments of the present invention are well suited for fabrication as microfluidic devices. FIG. 4 depicts a microfluidic device, generally designated by the numeral 311, having features of common to those depicted in FIG. 2 such that common elements will bear similar numeric designations. Device 311 has a primary conduit 115 having or in the form of a first arm, generally designated by the numeral 151. The first arm 151 has a first length, first distal end 153, and a first proximal end 155. The first length is the distance between the first proximal end 155 and the first distal end 153. The first proximal end 155 is attached to or constructed and arranged to attach to a base [not shown]. The first distal end 153 is free for vibrating at a resonant frequency determined by the mass of the primary conduit and solutions carried therein. The distal end 153 corresponds to the motion point 129.

Device 311 is planar made as a chip, tile or solid flat form of metal, ceramic and or plastic. The device 311 is made by molding, bonding layers, or the like. By way of example, without limitation, the device 311 is made by creating one of more top and bottom layers and one or more middle layers. The middle layers have fluidic patterns and are subsequently bonded, welded or glued to the top and bottom layers.

A metallized strip 173 is secured to the section of device 311 toward distal end 153 to cooperate with energy means and determining means to be discussed more fully below.

Figure 5:
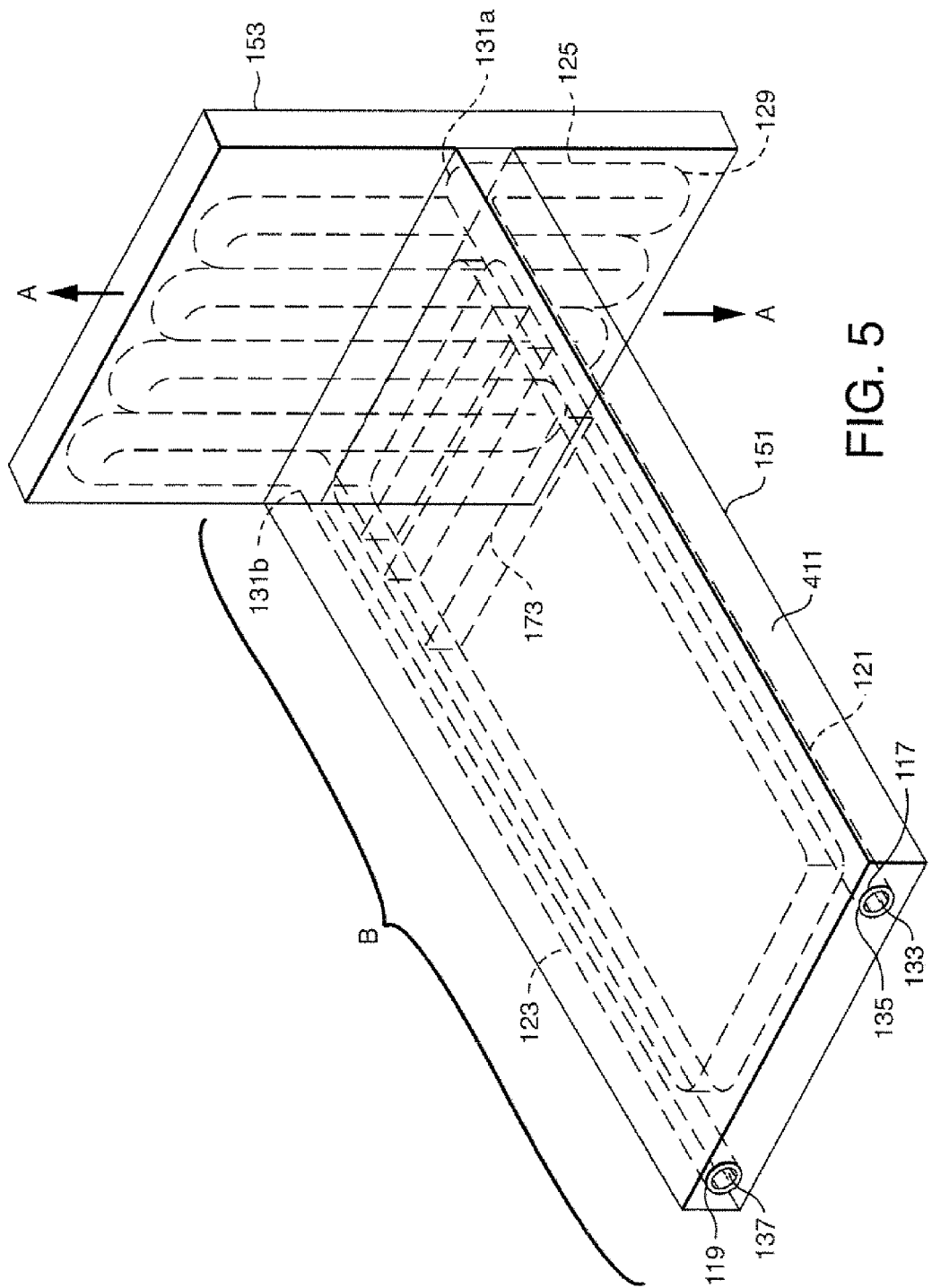
FIG. 5 depicts a device, in partial cross section, embodying features of the present invention; and, FIG. 6 depicts a device embodying features of the present invention.

FIG. 5 depicts a microfluidic device, generally designated by the numeral 411, having features of common to those depicted in FIG. 3 such that common elements will bear similar numeric designations. Device 411 has a primary conduit 115 having or in the form of a first arm, generally designated by the numeral 151. The first arm 151 has a first length, first distal end 153, and a first proximal end 155. The first length is the distance between the first proximal end 155 and the first distal end 153 denoted by bracket B. The first proximal end 155 is attached to or constructed and arranged to attach to a base [not shown]. The first distal end 153 is free for vibrating at a resonant frequency determined by the mass of the primary conduit and solutions carried therein. The distal end 153 corresponds to the motion point 129.

Device 411 is bi-planar made as a chip, tile or solid flat form or a group of chips, tiles or flat forms. Again, the device is comprised of metal, ceramic and/or plastic. The device 311 has an analytical section 125 in a plane corresponding to the tangent of the arc of the motion point 129. The arc is denoted by arrows A-A. The device 411 can be made as a unitary structure or the analytical section 125 may be made separately from the first flex section 121 and second flex section 123 in the manner previously described. And, after the two sections are formed, they are combined and bonded, welded or glued as depicted in FIG. 5.

Figure 6:
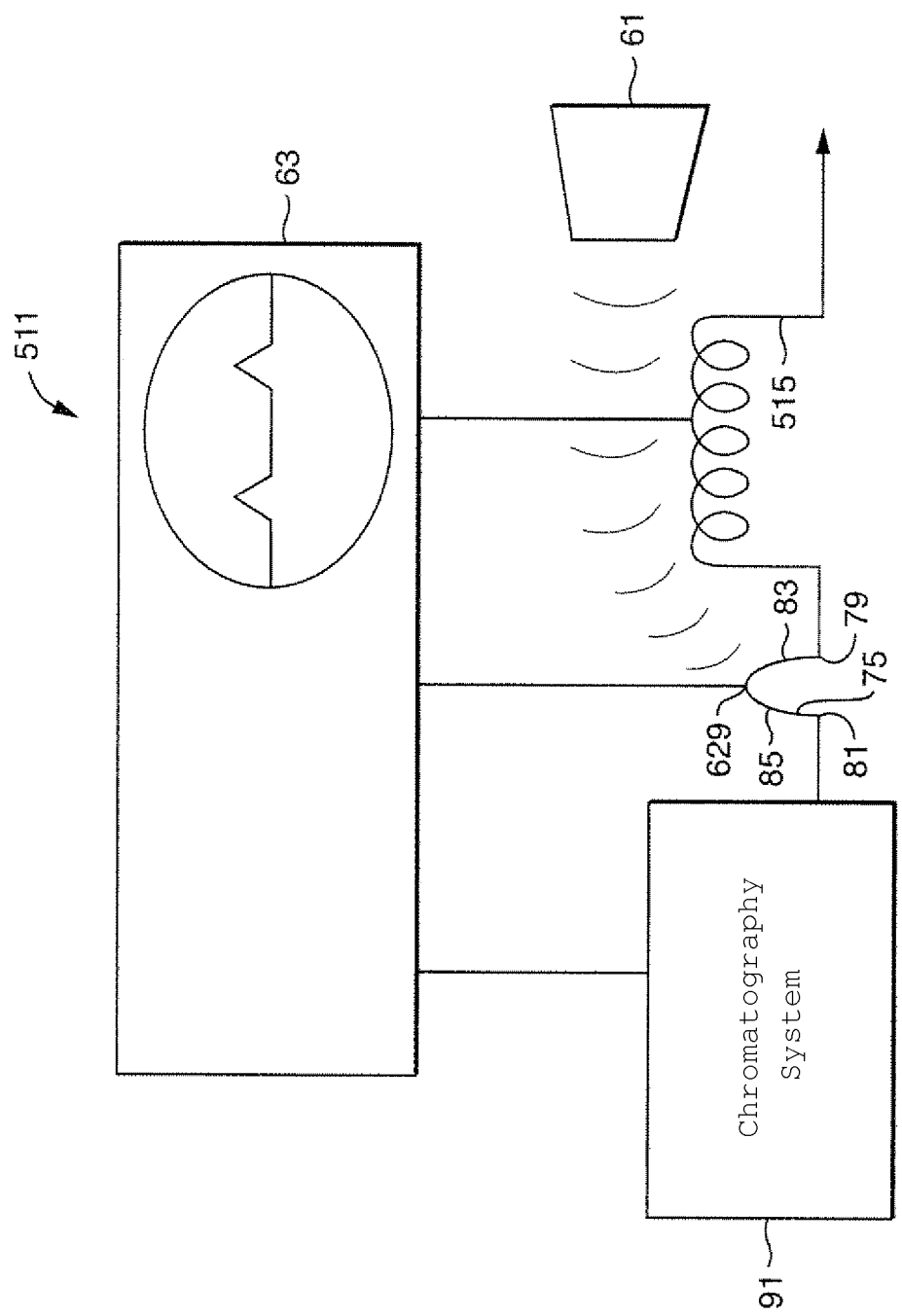

Turning now to FIG. 6, a device generally designated by the numeral 511, embodying features of the present invention is depicted. The device 511 has a primary conduit 515 which may comprise any of the forms describe thus far. The device 511 further comprises energy means 61 for inducing vibration in the first arm. As used herein, energy means 61 comprise mechanical, electrical, optical, acoustic, and magnetic mechanisms for imparting kinetic energy to the primary conduit 515 setting the primary conduit in motion. Depending on the form of energy means, the primary conduit 515 will be affixed to suitable cooperating elements to receive the energy. By way of example, without limitation, electro-magnetic energy means may require a metallized strip 173 as shown in FIGS. 4 and 5, magnetic strip or wires whereas optical or thermal energy means may have light or heat receiving surfaces.

The primary conduit 515, in response to the periodic application of such energy, will exhibit a resonant frequency in which the energy to induce and maintain such motion is most efficient, the resonant frequency.

Device 511 further comprises determining means 63 for determining a resonant frequency of the primary conduit 515. The determining means 63 for determining the resonant frequency is preferably in signal communication with the energy means 61 for inducing vibration in the primary conduit 515. For example, without limitation, the determining means 63 monitors and/or controls the phase difference between the energy means and the sensing devices detect the motion. Thus, determining means 63 comprises sensors for detecting the movement of the primary 63 conduit 515 and/or energy consumption of the energy means 61. The determining means further comprises computational processing units (CPUs) for processing the signals and data. The CPUs may be integral to existing equipment or associated with a free standing computer-type device such as a personal computer, mainframe computer or server.

Preferably, determining means 63 compares the resonant frequency or the energy consumption of the primary conduit 515 in the presence or potential presence of an analyte and compares the value to a standard. The comparison relates to the density and/or mass of one or more solutions flowing through the first channel.

One preferred device 511 features a primary conduit 515 as described and further comprises a secondary conduit 75. The secondary conduit 75 is in fluid communication with the primary conduit 515. As used herein, the term "fluid communication" means commonly plumbed.

The secondary conduit 75 has a secondary first fixed end 79, a secondary second fixed end 81, at least one secondary first flex section 83 and at least one secondary second flex section 85. The secondary first fixed end 81 and the secondary second fixed end 83 are each for attachment to a base [not shown]. The secondary first flex section 83 has a secondary flex section length and, similarly, the secondary second flex section 85 has a secondary second flex section length. The secondary first flex section 83 and secondary second flex section 85 define a secondary motion point 629 distal to the secondary first end 83 and the secondary second end 85 in which the secondary conduit has the greatest degree of motion. The motion point 629 is for vibrating at a resonant frequency determined by the mass of the secondary conduit and solutions carried with the secondary conduit.

The secondary conduit has a secondary channel [not shown] in the nature of the first channel 33 described in previous embodiments of the primary conduit. The passage defines a fluid path for receiving the solutions. And, the secondary channel has a secondary inlet and a secondary outlet. The first inlet is at the secondary first fixed end and the first outlet at the secondary second fixed end. The secondary analysis section spans therebetween and defines a secondary channel volume. The volume of the second channel may be the same or different that the volume of the first channel Preferably, the second conduit 75 allows measurement of at least one mass parameter of a solution in which the analyte is the present in one of the first channel and second channel and absent in the other. Thus, the difference in mass of the analyte can be directly related to the differences in resonance of the primary conduit 515.

The device 511 further comprise energy means [not shown], in the nature previously described with respect to the primary conduit 515, for inducing vibration in said second conduit 75. And, the device further comprises determining means [not shown] for determining the resonant frequency of said second conduit 75 in the nature of that previously described with primary conduit 515.

An additional benefit to the use of one or more secondary volumes is that signals that may result from external extraneous influences are more easily rejected.

As depicted, device 511 further comprises a chromatography system 91 for separating samples into concentrations of compounds identified on detectors as peaks. The chromatography system is in fluid communication first with the secondary conduit 75 and then the primary conduit 515. The secondary conduit 75 receives the fluid from the chromatography system and identified the peak of compounds. The peak so identified allows the primary conduit 515 to relate the presence of the peak to a mass represented by the change in resonance.

Preferably, such determining means determines a small mass change related to the presence of an analyte in accordance with the equation:

$$\frac{\delta \omega_0}{\omega_0} \propto -\frac{\delta m}{m}$$

Where $\omega_0$ is the resonant frequency of the device in the absence of analyte, $\delta \omega_0$ is the change in resonant frequency observed when an analyte is present within the device, m is the mass of the device and $\delta m$ is the change in mass of the device when analyte is present.

A further embodiment of the present invention, directed to a method for measuring changes in a solution, will be described with respect to the operation of the device depicted in FIGS. 3 and 6. In operation, a device 211, having a primary conduit 115 having a first fixed end 117, second fixed end 119, at least one first flex section 121, at least one second flex section 123 and at least one analytical section 125. The first fixed end 117 and the second fixed end 119 are each for attachment to a base [not shown]. The first flex section 117 has a first flex section length and, similarly, the second flex section 119 has a second flex section length. The first flex section 117 and second flex section 119 define a motion point 129 distal to the first end 117 and the second end 119 in which the primary conduit 115 has the greatest degree of motion. The motion point 129 is for vibrating at a resonant frequency determined by the mass of the primary conduit 115 and solutions carried with the primary conduit 115. The primary conduit 115 has a first channel 133 defining a fluid path for receiving solutions. The first channel has an inlet and an outlet. The first inlet is at the first fixed end 117 and the first outlet at the second fixed end 119. The first analysis section 125 has at least one curve comprising the first channel 133 about the motion point 129 and having an analysis length. The analysis length exceeds at least one half of one of the first conduit length and said second conduit length. The first conduit 115 is for cooperating, referring now to FIG. 6, with energy means 61 for inducing vibration and determining means 63 for determining a resonant frequency to calculate a mass related parameter of the solution carried therein. The method further comprises the step of inducing vibration of the primary conduit 115 and determining a resonant frequency of the first conduit 115 as a function of the solutions flowing there through.

In conjunction with high performance liquid chromatography, referring back to FIG. 3, the first analysis section 125 has a first analysis section volume and the first analysis section volume corresponds to a high performance liquid chromatography peak volume of the analyte to focus the peak in such first analysis section 125.

Returning now to FIG. 6, the device 511 having a primary conduit 515 and a secondary conduit 75, utilizes the secondary conduit 75 to identify the volume of the flow corresponding to the peak and potentially as a reference standard. That is, where the primary conduit 515 and secondary conduit 75 are similar in configuration, one conduit can be used as a reference standard to the other as sample pass through.

The mass of an analyte is calculated in accordance with the equation:

$$\frac{\delta\omega_0}{\omega_0} \propto -\frac{\delta m}{m}$$

Where $\omega_0$ is the resonant frequency of the device in the absence of analyte, $\delta\omega_0$ is the change in resonant frequency observed when an analyte is present within the device, m is the mass of the device and $\delta m$ is the change in mass of the device when analyte is present.

Determining means 63 is preferably programmed to make such calculation.

These and other features and advantages of the present invention will be apparent to those skilled in the art upon viewing the drawing and reading the detailed descriptions that follow.

What is claimed:

1. A device, for performing an analysis of a solution, comprising:
    a primary conduit having a first fixed end, second fixed end, at least one first flex section, at least one second flex section and at least one analysis section, said first fixed end and said second fixed end each for attachment to a base and said first flex section having a first flex section length and second flex section having a second flex section length, said first flex section and second flex section defining a motion point distal to said first end and said second end in which said primary conduit has the greatest degree of motion, said motion point for vibrating at a resonant frequency determined by the mass of said primary conduit and solutions carried with said primary conduit, wherein the motion point moves in an arc and the analysis section is substantially tangential to the arc of movement of the motion point;
    said primary conduit having a first channel defining a fluid path for receiving said solutions, said first channel having an inlet, an outlet, said first inlet at said first fixed end and said first outlet at said second fixed end, said first analysis section having at least one curve comprising a first channel about said motion point and having an analysis length, said analysis length exceeding at least one half of one of the first flex section length and said second flex section length;
    said primary conduit for cooperating with means for inducing vibration and means for determining a resonant frequency to calculate a mass related parameter of the solution carried therein.

2. The device of claim 1 wherein said analysis length is at least as long as one of said first conduit length and second conduit length.

3. The device of claim 1 wherein said primary conduit has a first arm having a first distal end, a first proximal end and an arm length, said first proximal end for attachment to a base, said first flex section and said second flex section carried on said arm length and said first distal end at about said motion point for vibrating at a resonant frequency determined by the mass of said primary conduit and solutions carried with said primary conduit.

4. The device of claim 1 further comprising energy means for inducing vibration in said primary conduit and capable of being placed in signal communication with said means for determining a resonant frequency of said primary conduit for placing vibration energy in said primary conduit.

5. The device of claim 1 further comprising determining means for determining the resonant frequency of said primary conduit, said determining means in signal communication with said energy means for inducing vibration in said primary conduit and comparing said resonant frequency to a standard to determine the density and/or mass of one or more solutions flow there through.

6. The device of claim 1 wherein said analysis section comprises a coil of channel.

7. The device of claim 1 wherein said analysis section comprises a serpentine pattern of channel.

8. The device of claim 1 wherein the internal diameter of said primary conduit in said analysis section is larger than the internal diameter of said primary conduit within said flex sections.

9. The device of claim 1 wherein said analysis section has an analysis section volume and said analysis section volume corresponds to a fraction of a high performance liquid chromatography peak volume of said analyte to focus said peak in said analysis section.

10. The device of claim 9 wherein said analysis section is larger than the anticipated peak of said analyte.

11. The device of claim 10 wherein said analysis section is five to ten percent larger than the anticipated peak.

12. The device of claim 11 further comprising a chromatographic system.

13. The device of claim 9 further comprising a secondary conduit, said secondary conduit in fluid communication with said primary conduit, said secondary conduit having a secondary first fixed end, a secondary second fixed end and at least one secondary first flex section and at least one secondary second flex section, said secondary first fixed end and said secondary second fixed end each for attachment to a base and said secondary flex section having a secondary flex section length and secondary second flex section having a secondary second flex section length, said secondary first flex section and secondary second flex section defining a secondary motion point distal to said secondary first end and said secondary second end in which said secondary conduit has the greatest degree of motion, said motion point for vibrating at a resonant frequency determined by the mass of said secondary conduit and solutions carried with said secondary conduit; said secondary conduit having a secondary channel defining a fluid path for receiving said solutions, said secondary channel having an secondary inlet, an secondary outlet, and at least one secondary analysis section, said first inlet at said first fixed end and said first outlet at said second fixed end, said secondary analysis section spanning therebetween and defining a secondary channel volume said second channel volume smaller than the volume of said primary analysis section to allow measurement of mass parameters of a solution in the presence and absence of a peak in said first channel and said second channel.

14. The device of claim 13 further comprising energy means for inducing vibration in said secondary conduit.

15. The device of claim 14 further comprising determining means for determining the resonant frequency of said secondary conduit.

16. The device of claim 15 wherein said determining means compares said resonant frequency of said secondary conduit to said resonant frequency of said primary conduit to determine the mass of one or more analytes.

17. The device of claim 16 wherein said determining means for determining the resonant frequency determines a mass for an analyte in accordance with the equation:

$$\frac{\delta\omega_0}{\omega_0} \propto -\frac{\delta m}{m}$$

Where $\omega_0$ is the resonant frequency of the device in the absence of analyte, $\delta\omega_0$ is the change in resonant frequency observed when an analyte is present within the device, m is the mass of the device and $\delta m$ is the change in mass of the device when analyte is present.

18. The device of claim 1, further comprising one or more cross-members attached between the at least one first flex section and the at least one second flex section, the one or more cross-members configured to reduce twisting modes of vibration in which the at least one first flex section and the at least one second flex section move in opposite directions.

19. A method for measuring changes in a solution comprising the steps of
providing a device having a primary conduit having a first fixed end, second fixed end, at least one first flex section, at least one second flex section and at least one first analysis section, said first fixed end and said second fixed end each for attachment to a base and said first flex section having a first flex section length and second flex section having a second flex section length, said first flex section and second flex section defining a motion point distal to said first end and said second end in which said primary conduit has the greatest degree of motion, said motion point for vibrating at a resonant frequency determined by the mass of said primary conduit and solutions carried with said primary conduit, wherein the motion point moves in an arc and the analysis section is substantially tangential to the arc of movement of the motion point;
said primary conduit having a first channel defining a fluid path for receiving said solutions, said first channel having an inlet, an outlet, said first inlet at said first fixed end and said first outlet at said second fixed end, said first analysis section having at least one curve comprising a first channel about said motion point and having an analysis length, said analysis length exceeding at least one half of one of the first flex section length and said second flex section length;
said primary conduit for cooperating with means for inducing vibration and means for determining a resonant frequency to calculate a mass related parameter of the solution carried therein; and
inducing vibration of said primary conduit and determining a resonant frequency of said primary conduit as a function of the solutions flowing there through.

20. The method of claim 19 wherein said analysis length is at least as long as one of said first conduit length and second conduit length.

21. The method of claim 19 wherein said primary conduit has a first arm having a first distal end, a first proximal end and an arm length, said first proximal end for attachment to a base, said first flex section and said second flex section carried on said arm length and said first distal end at about said motion point for vibrating at a resonant frequency determined by the mass of said primary conduit and solutions carried with said primary conduit.

22. The method of claim 19 wherein said device further comprises energy means for inducing vibration in said primary conduit and capable of being placed in signal communication with said means for determining a resonant frequency of said primary conduit for placing vibration energy.

23. The method of claim 19 further comprising determining means for determining the resonant frequency of said primary conduit, said determining means in signal communication with said energy means for inducing vibration in said primary conduit and comparing said resonant frequency to a standard to determine the density and/or mass of one or more solutions flow there through.

24. The method of claim 19 wherein said analysis section comprises a coil of channel.

25. The method of claim 19 wherein said analysis section comprises a serpentine pattern of channel.

26. The method of claim 19 wherein said analysis section has an analysis section volume and said analysis section volume corresponds to a high performance liquid chromatography peak volume of said analyte to focus said peak in said analysis section.

27. The method of claim 26 wherein said analysis section is larger than the anticipated peak of said analyte.

28. The method of claim 27 wherein said analysis section is five to ten percent larger than the anticipated peak.

29. The method of claim 26 wherein said device further comprises a secondary conduit said secondary conduit, in fluid communication with said primary conduit, said secondary conduit having a secondary first fixed end, a secondary second fixed end and at least one secondary first flex section and at least one secondary second flex section, said secondary first fixed end and said secondary second fixed end each for attachment to a base and said secondary flex section having a secondary flex section length and secondary second flex section having a secondary second flex section length, said secondary first flex section and secondary second flex section defining a secondary motion point distal to said secondary first end and said secondary second end in which said secondary conduit has the greatest degree of motion, said motion point for vibrating at a resonant frequency determined by the mass of said secondary conduit and solutions carried with said secondary conduit; said secondary conduit having a secondary channel defining a fluid path for receiving said solutions, said secondary channel having an secondary inlet, an secondary outlet, and at least one secondary analysis section, said first inlet at said first fixed end and said first outlet at said second fixed end, said secondary analysis section spanning therebetween and defining a secondary channel volume said second channel volume smaller than the volume of said primary analysis section to allow measurement of mass parameters of a solution in the presence and absence of a peak in said first channel and said second channel; and
identifying at least one peak in said secondary conduit to allow determinations as to the mass of an analyte.

30. The method of claim 29 wherein said device further comprising energy means for inducing vibration in said secondary conduit.

31. The method of claim 29 wherein said device further comprises determining means for determining the resonant frequency of said secondary conduit.

32. The method of claim 31 wherein said determining means compares said resonant frequency of said secondary conduit to said resonant frequency of said primary conduit to determine the mass of one or more analytes.

33. The method of claim 32 wherein said determining means for determining the resonant frequency determines a mass for an analyte in accordance with the equation:

$$\frac{\delta\omega_0}{\omega_0} \propto -\frac{\delta m}{m}$$

Where $\omega_0$ is the resonant frequency of the device in the absence of analyte, $\delta\omega_0$ is the change in resonant frequency observed when an analyte is present within the device, m is the mass of the device and $\delta m$ is the change in mass of the device when analyte is present.

34. The method of claim 19, wherein the device further comprises one or more cross-members attached between the at least one first flex section and the at least one second flex section, the one or more cross-members configured to reduce twisting modes of vibration in which the at least one first flex section and the at least one second flex section move in opposite directions.

* * * * *